(12) United States Patent
Misra

(10) Patent No.: US 6,448,264 B2
(45) Date of Patent: Sep. 10, 2002

(54) USE OF 5-THIO-, SULFINYL- AND SULFONYLPYRAZOLO[3,4-B]-PYRIDINES AS CYCLIN DEPENDENT KINASE INHIBITORS

(75) Inventor: Raj N. Misra, Hopewell, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/841,668

(22) Filed: Apr. 24, 2001

Related U.S. Application Data

(60) Provisional application No. 60/199,475, filed on Apr. 25, 2000.

(51) Int. Cl.[7] .................... A61K 31/435; C07D 471/04
(52) U.S. Cl. ....................................... 514/303; 546/119
(58) Field of Search ............................ 546/119; 514/303

(56) References Cited

U.S. PATENT DOCUMENTS

| | | | |
|---|---|---|---|
| 3,903,096 A | * 9/1975 | Denzel et al. | ............... 546/119 |
| 6,107,305 A | 8/2000 | Misra et al. | ................. 514/303 |

FOREIGN PATENT DOCUMENTS

| WO | WO 95/34563 | 12/1995 |
|---|---|---|
| WO | WO 99/30710 | 6/1999 |
| WO | WO 00/69846 | 11/2000 |
| WO | WO 01/02369 A2 | 1/2001 |
| WO | WO 01/12188 A1 | 2/2001 |
| WO | WO 01/12189 A1 | 2/2001 |

\* cited by examiner

*Primary Examiner*—Bernard Dentz
(74) *Attorney, Agent, or Firm*—Rena Patel

(57) ABSTRACT

The present invention describes compounds of formula (I):

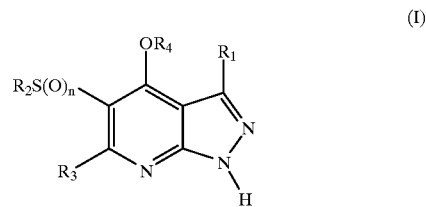

and pharmaceutically acceptable salts thereof, wherein $R^1$, $R^2$, $R^3$, $R^4$ and n are as defined above. Compounds of formula (I) are protein kinase inhibitors and are useful in the treatment of proliferative diseases, for example, cancer, inflammation and arthritis. They may also be useful in the treatment of Alzheimer's disease and cardiovascular disease.

29 Claims, No Drawings

USE OF 5-THIO-, SULFINYL- AND SULFONYLPYRAZOLO[3,4-B]-PYRIDINES AS CYCLIN DEPENDENT KINASE INHIBITORS

This application claims priority from provisional application Ser. No. 60/199,475, filed Apr. 25, 2000, incorporated herein by reference in its entirety.

FIELD OF THE INVENTION

The present invention relates to inhibitors of cyclin dependent kinase and their use in the treatment of proliferative diseases.

BACKGROUND OF THE INVENTION

Normal cellular proliferation is stringently regulated by a series of proteins that constitute the cell cycle machinery. Proteins that play a key role in controlling cell cycle progression are the cyclin dependent kinases (CDKs). CDKs are serine/threonine protein kinases that are the driving force behind the cell cycle and cell proliferation. The active CDK enzyme is a multi-subunit complex composed of at least one catalytic (CDK) subunit and one regulatory (cyclin) subunit. See, Brooks and La Thangue, DDT, 4, 455–464 (1999). It has been found that inhibitors of CDK activity are effective for the treatment of proliferative diseases (e.g. cancer). See, Webster and Kimball, Emerging Drugs, 5, 45–59 (2000).

SUMMARY OF THE INVENTION

The present invention is directed to the use of compounds of formula

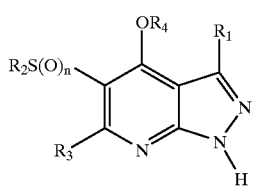

(I)

and pharmaceutically acceptable salts thereof as inhibitors of cyclin dependent kinases. As used in formula I, and throughout the specification, the symbols have the following meanings:

$R_1$ is hydrogen, aryl or lower alkyl;

$R_2$ and $R_4$ are each independently alkyl, aryl, arylalkyl, heteroaryl, heteroarylalkyl, cycloalkyl, cycloalkylalkyl, heterocycloalkyl or heterocycloalkylalkyl;

$R_3$ is hydrogen or lower alkyl; and n is an integer of 0, 1 or 2.

The compounds of formula I are protein kinase inhibitors and are useful in the treatment and prevention of proliferative diseases, for example, cancer, inflammation and arthritis. They may also be useful in the treatment of neurodegenerative diseases such Alzheimer's disease, cardiovascular diseases, viral diseases and fungal diseases.

DETAILED DESCRIPTION OF THE INVENTION

The present invention provides for a method of using compounds of formula I as inhibitors of cyclin dependent kinases, which are active in the treatment of proliferative diseases, such as for example, but not limited to, cancer, Alzheimer's disease, arthritis, inflammation, and cardiovascular disease. The present invention also contemplates pharmaceutical compositions employing such compounds.

Listed below are definitions of various terms used to describe the compounds of the instant invention. These definitions apply to the terms as they are used throughout the specification (unless they are otherwise limited in specific instances) either individually or as part of a larger group.

It should be noted that any heteroatom with unsatisfied valences is assumed to have hydrogen atoms sufficient to satisfy the valences.

Carboxylate anion refers to a negatively charged group —COO$^-$.

The term "alkyl" or "alk" refers to a monovalent alkane (hydrocarbon) derived radical containing from 1 to 12 carbon atoms unless otherwise defined. The term "lower alkyl" refers to an alkyl group of 1 to 6 carbon atoms. An alkyl group is an optionally substituted straight, branched or cyclic saturated hydrocarbon group. When substituted, alkyl groups may be substituted with up to four substituent groups, as defined below, at any available point of attachment. When the alkyl group is said to be substituted with an alkyl group, this is used interchangeably with "branched alkyl group". Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituent groups (or substituents) may include, but are not limited to, one or more of the following groups: halo (such as F, Cl, Br or I), haloalkyl (such as CCl$_3$ or CF$_3$), alkoxy, aryloxy, alkyl S(O)$_m$ (m=0, 1, 2), aryl S(O)$_m$ (m=0, 1, 2), hydroxy, carboxy (—COOH), alkyloxycarbonyl (—COOR'), alkylcarbonyloxy (—OCOR'), amino (—NH$_2$), quaternary nitrogen, carbamoyl (—NHCOOR'— or —OCONHR'—), urea (—NHCONHR'—), thiol (—SH), cyano or nitro. Alkyl groups as defined may also comprise one or more carbon to carbon double bonds or one or more carbon to carbon triple bonds.

The term "alkenyl" refers to a hydrocarbon radical straight, branched or cyclic containing from 2 to 12 carbon atoms and at least one carbon to carbon double bond.

The term "alkynyl" refers to a hydrocarbon radical straight, branched or cyclic containing from 2 to 12 carbon atoms and at least one carbon to carbon triple bond.

Cycloalkyl is a type of alkyl containing from 3 to 15 carbon atoms, without alternating or resonating double bonds between carbon atoms. It may contain from 1 to 4 rings. Exemplary unsubstituted such groups include cyclopropyl, cyclobutyl, cyclopentyl, cyclohexyl, etc. Exemplary substituents include one or more of the following groups: halogen, alkyl, alkoxy, alkyl hydroxy, amino, nitro, cyano, thiol and/or alkylthio.

The terms "alkoxy" or "alkylthio", as used herein, denote an alkyl group as described above bonded through an oxygen linkage (—O—) or a sulfur linkage (—S—), respectively.

The term "alkyloxycarbonyl", as used herein, denotes an alkoxy group bonded through a carbonyl group. An alkoxycarbonyl radical is represented by the formula —C(O)OR, where the R group is a straight or branched C$_{1-6}$ alkyl group.

The term "alkylcarbonyl" refers to an alkyl group bonded through a carbonyl group.

The term "alkylcarbonyloxy", as used herein, denotes an alkylcarbonyl group which is bonded through an oxygen linkage.

The term "arylalkyl", as used herein, denotes an aromatic ring bonded through an alkyl group as described above.

The term "aryl" refers to monocyclic or bicyclic aromatic rings, e.g., phenyl, substituted phenyl and the like, as well as groups which are fused, e.g., napthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Aryl groups may optionally be substituted with one or more groups including, but not limited to, halogen, alkyl, alkoxy, hydroxy, carboxy, carbamoyl, alkyloxycarbonyl, nitro, trifluoromethyl, amino, cycloalkyl, cyano, alkylS(O)$_m$ (m=0, 1, 2), or thiol.

The term "heteroaryl" refers to a monocyclic aromatic hydrocarbon group having 5 or 6 ring atoms, or a bicyclic aromatic group having 8 to 10 atoms, containing at least one heteroatom, O, S, or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Additional nitrogen atoms may be present together with the first nitrogen and oxygen or sulfur. Exemplary heteroaryl groups include the following: thienyl, furyl, pyrrolyl, pyridinyl, imidazolyl, pyrrolidinyl, piperidinyl, thiazolyl, oxazolyl, triazolyl, pyrazolyl, isoxazolyl, isothiazolyl, pyrazinyl, pyridazinyl, pyrimidinal, triazinylazepinyl, indolyl, isoindolyl, quinolinyl, isoquinolinyl, benzothiazolyl, benzoxazolyl, benzimidazolyl, benzoxadiazolyl, benzofurazanyl and tetrahydropyranyl. Exemplary substituents include one or more of the following: halo, alkyl, alkoxy, hydroxy, cycloalkyl, nitro, cyano, amino, alkylS(O)$_m$ (m=0, 1, 2), or thiol. The term "heteroarylalkyl", as used herein denotes a heteroaryl ring bonded through an alkyl group as described hereinabove.

The term "heteroarylium" refers to heteroaryl groups bearing a quaternary nitrogen atom and thus a positive charge.

The term "heterocycloalkyl" refers to a cycloalkyl group (nonaromatic) in which one of the carbon atoms in the ring is replaced by a heteroatom selected from O, S or N, and in which up to three additional carbon atoms may be replaced by said heteroatoms. In addition, the sulfur may be oxidated to the sulfone (—SO$_2$—) or sulfoxide (—SO—) and the nitrogen may be quaternary.

The term "quaternary nitrogen" refers to a tetravalent positively charged nitrogen atom including, e.g., the positively charged nitrogen in a tetraalkylammonium group (e.g., tetramethylammonium, N-methylpyridinium), the positively charged nitrogen in protonated ammonium species (e.g., trimethylhydroammonium, N-hydropyridinium), the positively charged nitrogen in amine N-oxides (e.g. N-methyl-morpholine-N-oxide, pyridine-N-oxide), and the positively charged nitrogen in an N-amino-ammonium group (e.g., N-aminopyridinium).

The term "heteroatom" means O, S, P or N, selected on an independent basis.

The term "halogen" or "halo" refers to chlorine, bromine, fluorine or iodine.

The term "PMB" refers to para-methoxybenzyl.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al., *Protective Groups in Organic Synthesis*, Wiley, N.Y. (1991).

Suitable examples of salts of the compounds according to the invention with inorganic or organic acids are hydrochloride, hydrobromide, sulfate, phosphate. Salts which are unsuitable for pharmaceutical uses but which can be employed, for example, for the isolation or purification of free compounds I or their pharmaceutically acceptable salts, are also included.

All stereoisomers of the compounds of the instant invention are contemplated, either in admixture or in pure or substantially pure form. The definition of the compounds according to the invention embraces all possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates by conventional methods, such as, for example, salt formation with an optically active acid followed by crystallization.

It should be understood that the present invention includes prodrug forms of the compounds of formula I. Various forms of prodrugs are well known in the art. Examples of such prodrug derivatives are provided in the following references:

(a) *Design of Prodrugs*, edited by H. Bundgaard (Elsevier, 1985); and *Methods in Enzymology*, Vol. 42, pp. 309–396, edited by K. Widder et al., (Academic Press, 1985);

(b) *A Textbook of Drug Design and Development*, edited by Krosgaard-Larsen and H. Bundgaard, Chapter 5, "Design and Application of Prodrugs," by H. Bundgaard, pp. 113–191 (1991);

(c) H. Bundgaard, *Advanced Drug Delivery Reviews*, 8, pp. 1–38 (1992);

(d) H. Bundgaard et al., *Journal of Pharmaceutical Sciences*, 77, 285 (1988); and (e) N. Kayeka et al., *Chem. Phar. Bull.*, 32, 692 (1984).

It should be understood that solvates (e.g., hydrates) of the compounds of formula I are also within the scope of the present invention. Methods of solvation are generally known in the art. Accordingly, the compounds of the instant invention may be in the free or hydrate form, and may be obtained by methods exemplified by the following schemes.

Compounds of formula I for use as inhibitors of cyclin dependent kinases can be prepared by reacting a compound of formula II

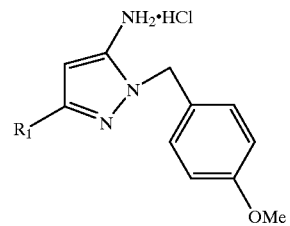

(II)

with a base such as sodium hydroxide or sodium carbonate to give a free base of formula IIa

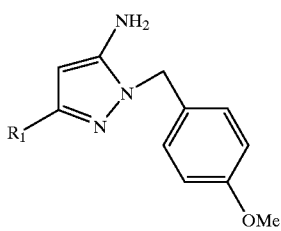

(IIa)

Compound IIa is reacted with a compound of formula III

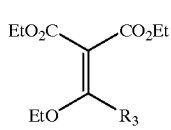

(III)

at an elevated temperature, preferably about 130° C., under reduced pressure to obtain compounds of formula IV

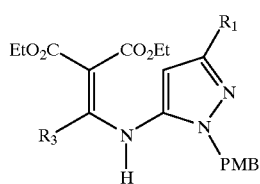

(IV)

The starting compound of formula II, where $R_1$ is hydrogen is prepared by reacting acrylonitrile with hydrazine hydrate in a solvent such as THF, followed by addition of p-methoxybenzaldehyde. The compound which results from this reaction is then reacted with a mixture of sodium n-butoxide in n-butanol followed by HCl to provide the key early intermediate of compound II.

Compounds of formula IV are then reacted at an elevated temperature, preferably from about 220° C. to 260° C., in the presence of a solvent such as diphenyl ether to obtain a compound of formula V

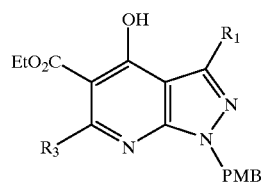

(V)

Compound V is then reacted with an aqueous base such as aqueous sodium hydroxide or aqueous potassium hydroxide at an elevated temperature, preferably about 95° C., to obtain a compound of formula VI

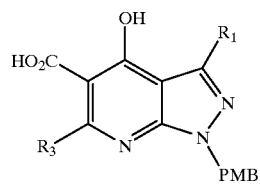

(VI)

Compound VI is stirred at an elevated temperature, preferably about 230° C., to obtain a compound of formula VII

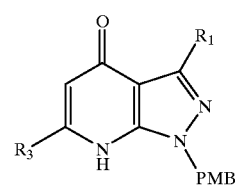

(VII)

The formula VII compound is reacted with bromine in the presence of a solvent such as ethanol, preferably at a temperature of about 0° C., to obtain a compound of formula VIII

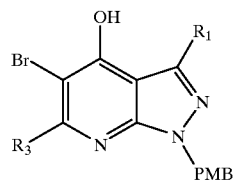

(VIII)

Compound VIII is then reacted with phosphorous oxychloride at a temperature from about 25° to 130 ° C. to obtain a compound of formula IX

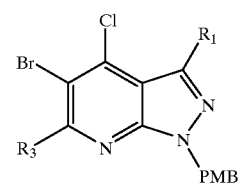

(IX)

Compound IX is reacted with a compound of formula X

MOR$_4$ (X)

wherein M is an alkali metal such as sodium or potassium, and $R_4$ is as described hereinabove in the presence of a solvent such as tetrahydrofuran, $R_4OH$ and the like at a temperature from about 25° C. to 90° C. to form a compound of formula XI

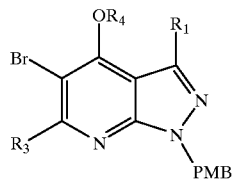
(XI)

The formula XI compound is reacted with an organolithium reagent such as n-butyllithium in a solvent such as tetrahydrofuran, ether and the like at a temperature from about −90° to −20° C. followed by treatment with a compound of formula XII $R_2SSR_2$ (XII)

wherein $R_2$ is as described hereinabove to obtain a compound of formula XIII

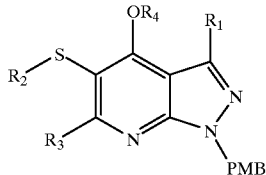
(XIII)

Compounds of formula XIII are then reacted with:

(1) an acid, such as trifluoroacetic acid (TFA), at a temperature from about 25° C. to 90° C., or
(2) hydrogen in the presence of a catalyst, such as palladium on carbon, to obtain compounds of formula I wherein n is 0

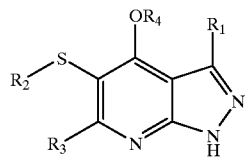

Compounds of formula I wherein n is 1 or 2 may be prepared by oxidizing compounds of formula I wherein n is 0 with an oxidizing agent such as m-chloroperoxybenzoic acid (mCPBA) and the like in the presence of a solvent such as dichloromethane. Generally one equivalent of the oxidizing agent is used to obtain compounds of formula I wherein n is 1, and two or more equivalents of the oxidizing agent are used to obtain compounds of formula I wherein n is 2.

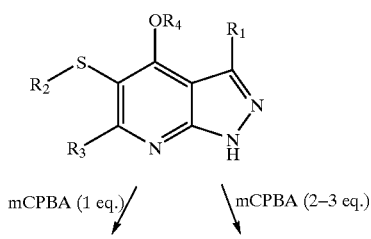

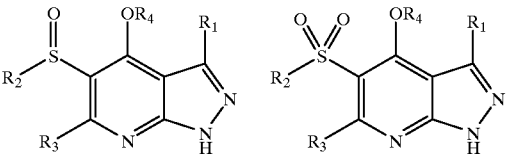

Intermediates of this invention may also be prepared by processes disclosed in U.S. Pat. Nos. 3,828,057, 3,966,746, 3,979,399, and 3,985,757 which are incorporated by reference herein. More specifically, intermediates of formula II may be prepared by procedures described in Hoehn, H., Z. Chem. 10, pp. 386–388 (1970).

Compounds of formulas II and III are commercially available or may be prepared by methods known to one of ordinary skill in the art.

All other compounds may be prepared by modification of the procedures described herein.

The preferred compounds of formula I are those wherein:

$R_1$ and $R_3$ are hydrogen;
$R_2$ is aryl or heteroaryl;
$R_4$ is alkyl, cycloalkyl or cycloalkylalkyl; and
n is an integer of 0, 1 or 2.

More preferred compounds of formula I are those wherein:

$R_1$ and $R_3$ are hydrogen;
$R_2$ is phenyl, 4-bromo-2,6-difluorophenyl, 4-chloro-2,6-difluorophenyl, 2,4,6-trifluorophenyl or 4-methyl-2,6-difluorophenyl;
$R_4$ is lower alkyl; and
n is 1.

The compounds according to the invention have pharmacological properties; in particular, the compounds of formula I are inhibitors of protein kinases such as the cyclin dependent kinases (cdks), for example, cdc2 (cdk1), cdk2, and cdk4. The novel compounds of formula I are expected to be useful in the therapy of proliferative diseases such as cancer, inflammation, arthritis, Alzheimer's disease and cardiovascular disease. These compounds may also be useful in the treatment of topical and systemic fungal infections.

More specifically, the compounds of formula I are useful in the treatment of a variety of cancers, including (but not limited to) the following:

carcinoma, including that of the bladder, breast, colon, kidney, liver, lung, ovary, pancreas, stomach, cervix, thyroid, prostate, and skin;

hematopoietic tumors of lymphoid lineage, including acute lymphocytic leukemia, B-cell lymphoma, and Burkett's lymphoma;

hematopoietic tumors of myeloid lineage, including acute and chronic myelogenous leukemias and promyelocytic leukemia;

tumors of mesenchymal origin, including fibrosarcoma and rhabdomyosarcoma; and other tumors, including melanoma, seminoma, teratocarcinoma, osteosarcoma, neuroblastoma and glioma.

Due to the key role of cdks in the regulation of cellular proliferation in general, inhibitors could act as reversible cytostatic agents which may be useful in the treatment of any disease process which features abnormal cellular proliferation, e.g., neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, angiogenesis, and endotoxic shock.

Compounds of formula I may also be useful in the treatment of Alzheimer's disease, as suggested by the recent finding that cdk5 is involved in the phosphorylation of tau protein (*J. Biochem*, 117, 741–749 (1995)).

Compounds of formula I may also act as inhibitors of other protein kinases, e.g., protein kinase C, her2, rafl, MEK1, MAP kinase, EGF receptor, PDGF receptor, IGF receptor, PI3 kinase, wee1 kinase, Src, Ab1, VEGF, and 1ck, and thus be effective in the treatment of diseases associated with other protein kinases.

Compounds of formula I also induce or inhibit apoptosis, a physiological cell death process critical for normal development and homeostasis. Alterations of apoptotic pathways contribute to the pathogenesis of a variety of human diseases. Compounds of formula I, as modulators of apoptosis, will be useful in the treatment of a variety of human diseases with abberations in apoptosis including cancer (particularly, but not limited to, follicular lymphomas, carcinomas with p53 mutations, hormone dependent tumors of the breast, prostate and ovary, and precancerous lesions such as familial adenomatous polyposis), viral infections (including, but not limited to, herpesvirus, poxvirus, Epstein-Barr virus, Sindbis virus and adenovirus), autoimmune diseases (including, but not limited to, systemic lupus, erythematosus, immune mediated glomerulonephritis, rheumatoid arthritis, psoriasis, inflammatory bowel diseases, and autoimmune diabetes mellitus), neurodegenerative disorders (including, but not limited to, Alzheimer's disease, AIDS-related dementia, Parkinson's disease, amyotrophic lateral sclerosis, retinitis pigmentosa, spinal muscular atrophy and cerebellar degeneration), AIDS, myelodysplastic syndromes, aplastic anemia, ischemic injury associated myocardial infarctions, stroke and reperfusion injury, arrhythmia, atherosclerosis, toxin-induced or alcohol induced liver diseases, hematological diseases (including, but not limited to, chronic anemia and aplastic anemia), degenerative diseases of the musculoskeletal system (including, but not limited to, osteoporosis and arthritis), aspirin-sensitive rhinosinusitis, cystic fibrosis, multiple sclerosis, kidney diseases, and cancer pain.

The compounds of this invention may also be useful in combination with known anti-cancer treatments such as radiation therapy or with cytostatic and cytotoxic agents, such as, for example, but not limited to, DNA interactive agents, such as cisplatin or doxorubicin; inhibitors of farnesyl protein transferase, such as those described in U.S. Pat. No. 6,011,029, topoisomerase II inhibitors, such as etoposide; topoisomerase I inhibitors, such as CPT-11 or topotecan; tubulin stabilizing agents, such as paclitaxel, docetaxel or the epothilones; hormonal agents, such as tamoxifen; thymidilate synthase inhibitors, such as 5-fluorouracil; and antimetabolites, such as methoxtrexate; antiangiogenic agents, such as angiostatin or endostatin; and kinase inhibitors, such as her2 specific antibodies. The formula I compounds of this invention may also be useful in combination with modulators of p53 transactivation. In addition, the formula I compounds may be used for treating chemotherapy-induced alopecia, chemotherapy-induced thrombocytopenia, chemotherapy-induced leukopenia or mucocitis. In the treatment of chemotherapy-induced alopecia, the formula I compound is preferably topically applied in the form of a medicament such as a gel, shampoo, aerosol, dust, cream, ointment, solution, dispersion or paste.

If formulated as a fixed dose, such combination products employ the compounds of this invention within the dosage range described below and the other pharmaceutically active agent within its approved dosage range. For example, the cdc2 inhibitor olomucine has been found to act synergistically with known cytotoxic agents in inducing apoptosis (*J. Cell Sci.*, 108, 2897 (1995)). Compounds of formula I may be used sequentially with known anti-cancer or cytotoxic agents when a combination formulation is inappropriate.

cdc2/cyclin B1 Kinase Assay cdc2/cyclin B1 kinase activity was determined by monitoring the incorporation of $^{32}p$ into histone HI. The reaction consisted of 50 ng baculovirus expressed GST-cdc2, 75 ng baculovirus expressed GST-cyclin B 1, 1 $\mu$g histone HI (Boehringer Mannheim), 0.2 $\mu$Ci of $^{32}p$ γ-ATP and 25 $\mu$M ATP in kinase buffer (50 mM Tris, pH 8.0, 10 mM $MgCl_2$, 1 mM EGTA, 0.5 mM DTT). The reaction was incubated at 30° C. for 30 minutes and then stopped by the addition of cold trichloroacetic acid (TCA) to a final concentration of 15% and incubated on ice for 20 minutes. The reaction was harvested onto GF/C unifilter plates (Packard) using a Packard Filtermate Universal harvester, and the filters were counted on a Packard TopCount 96-well liquid scintillation counter (Marshak, D. R., Vanderberg, M. T., Bae, Y. S., Yu, I. J., *J. Cellular Biochemistry*, 45, 391–400 (1991), incorporated by reference herein).

cdk2/cyclin E Kinase Assay cdk2/cyclin E kinase activity was determined by monitoring the incorporation of $^{32}p$ into the retinoblastoma protein. The reaction consisted of 2.5 ng baculovirus expressed GST-cdk2/cyclin E, 500 ng bacterially produced GST-retinoblastoma protein (aa 776–928), 0.2 $\mu$Ci $^{32}P$ γ-ATP and 25 $\mu$M ATP in kinase buffer (50 mM Hepes, pH 8.0, 10 mM $MgCl_2$, 5 mM EGTA, 2 mM DTT). The reaction was incubated at 30° C. for 30 minutes and then stopped by the addition of cold trichloroacetic acid (TCA) to a final concentration of 15% and incubated on ice for 20 minutes. The reaction was harvested onto GF/C unifilter plates (Packard) using a Packard Filtermate Universal harvester, and the filters were counted on a Packard TopCount 96-well liquid scintillation counter.

cdk4/cyclin D1 Kinase Activity cdk4/cyclin D1 kinase activity was determined by monitoring the incorporation of $^{32}p$ in to the retinoblastoma protein. The reaction consisted of 165 ng baculovirus expressed as GST-cdk4, 282 ng bacterially expressed as S-tag cyclin D1, 500 ng bacterially produced GST-retinoblastoma protein (aa 776–928), 0.2 $\mu$Ci $^{32}P$ γ-ATP and 25 $\mu$M ATP in kinase buffer (50 mM Hepes, pH 8.0, 10 mM $MgCl_2$, 5 mM EGTA, 2 mM DTT). The reaction was incubated at 30° C. for 1 hour and then stopped by the addition of cold trichloroacetic acid (TCA) to a final concentration of 15% and incubated on ice for 20 minutes. The reaction was harvested onto GF/C unifilter plates (Packard) using a Packard Filtermate Universal harvester, and the filters were counted on a Packard TopCount 96-well liquid scintillation counter (Coleman, K. G., Wautlet, B. S., Morissey, D, Mulheron, J. G., Sedman, S., Brinkley, P., Price, S., Webster, K. R. (1997) Identification of CDK4 Sequences involved in cyclin D, and p16 binding. *J. Biol. Chem.* 272,30:18869–18874, incorporated by reference herein).

Further subject matter of the invention also includes pharmaceuticals for use as described above including controlling cancer, inflammation and arthritis, which contain at least one compound of formula I as defined above or at least one of its pharmacologically acceptable acid addition salts, and the use of a compound of formula I as defined above for the preparation of a pharmaceutical having activity against proliferative diseases as described previously including against cancer, inflammation and/or arthritis.

The following examples are illustrative rather than limiting. It should be understood that there may be other embodiments which fall within the spirit and scope of the invention as defined by the claims appended hereto.

EXAMPLES

Example 1

1-(4-Butoxy-1H-pyrazolo[3,4-b]pyridin-5-yl)-1'-phenylsulfoxide

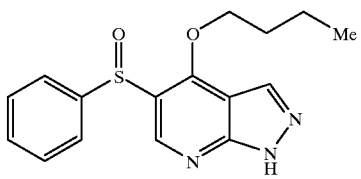

A. 4-Hydroxy-1-[(4-methoxyphenyl)methyl]-1H-pyrazolo[3,4-b]pyridine-5-carboxylic acid.

A solution of 5.20 g (15.9 mmol) of 4-hydroxy-1[(4-methoxyphenyl)methyl]-1H-pyrazolo[3,4-b]pyridine-5-carboxylic acid ethyl ester (see WO 99/30710 for preparation) in 20 mL of ethanol and 60 mL of 1M aq NaOH solution was stirred at 95° C. for 18 hr. The reation mixture was cooled to room temperature and acidified to pH=1 by addition of 1M aq HCl solution (~70 mL). A precipitate formed which was isolated by filtration. The solid was washed with water then dried under vacuum at 100° C. overnight to afford 4.48 g (94%) of Part A compound as a white solid, mp 220° C. (dec).

B. 1-[(4-Methoxyphenyl)methyl]-1H-pyrazolo[3,4-b]pyridin-4-one.

A 3.18 g (10.6 mmol) portion of Part A compound was heated under argon to 230° C. for 15 minutes. Upon heating the solid melted and gas evolution was observed. The material was cooled to room temperature to afford 2.71 g (100%) of Part B compound as an amber glass.

C. 5-Bromo-4-hydroxy-1-[(4-methoxyphenyl)methyl]-1H-pyrazolo[3,4-b]pyridine.

To a solution of 2.70 g (10.6 mmol) of part B compound in 60 mL of absolute ethanol cooled in an ice-bath was added dropwise a solution of 2.0 g (12 mmol) of bromine in 5 mL of ethanol over 5 min. A precipitate formed. The reaction was incomplete and after 1 hr an additional 0.3 mL of bromine was added. The mixture was stirred for an additional 1 hr then slowly 50 mL of 5% aq sodium bicarbonate solution was added. The reaction was warmed to room temperature and after 15 min concentrated in vacuo to give a slurry. The solid material was collected by filtration, washed with water then dried under vacuum at 90° C. overnight to give 3.43 g (97%) of Part C compound as a light beige solid, mp 209° C. (softens).

D. 5-Bromo-4-chloro-1-[(4-methoxyphenyl)methyl]-1H-pyrazolo[3,4-b]pyridine.

A mixture of 2.92 g (8.74 mmol) of Part C compound in 20 mL of phosphorous oxychloride was heated at 110° C. for 1 hr. The reaction mixture was cooled to room temperature then in an ice-bath and added slowly to 300 g of ice. After 15 min, 150 mL of EtOAc was added then slowly ~50 mL of 50% NaOH solution until the pH=7. The entire mixture was transferred to a separatory funnel. The aqueous layer was separated and extracted with 100 mL of EtOAc. The organic layers were combined, washed with 100 mL of brine, dried (sodium sulfate) and concentrated in vacuo then dried under vacuum at 90° C. to afford 2.94 g (95%) of Part D compound as a yellow-brown solid.

E. 5-Bromo-4-butoxy-1-[(4-methoxyphenyl)methyl]-1H-pyrazolo[3,4-b]pyridine.

The oil was removed from a 660 mg (60% in oil, 16 mmol) portion of sodium hydride dispersion by three washes with hexane then covered with 30 mL of dry THF. The mixture was heated to 50° then, in two portions, a total of 2.3 mL (25 mmol) of anhydrous n-butanol was added. The reaction mixture was stirred until gas evolution ceased, ~30 min, then cooled to room temperature. To the resulting solution was added 2.92 g (8.28 mmol) of Part D compound and stirred at 60° C. for 2 hr then cooled to room temperature and concentrated in vacuo to give a solid. The solid was partitioned between 50 mL of water and 50 mL of EtOAc. The organic layer was separated, washed with 50 mL of brine, dried (sodium sulfate) and concentrated in vacuo to give a brown solid. The crude solid was purified by flash chromatography (silica gel, 1:5 EtOAc/hexane) to afford 2.75 g (86%) of Part E compound as a white solid, mp 81–83° C.

F. 4-Butoxy-5-thiophenyl-1-[(4-methoxyphenyl)methyl]-1H-pyrazolo[3,4-b]pyridine.

To a solution of 195 mg (0.50 mmol) of Part E compound in 4 mL of dry THF cooled to −78° C. was added dropwise 0.30 mL (2.5M in hexane, 0.75 mmol) of n-butyllithium solution. After 0.5 hr a solution of 218 mg (1.0 mmol) of phenyl disulfide in 1 mL of THF was added. The reaction mixture was stirred at −78° C. for 6 hr then quenched by addition of aqueous sodium bisulfate solution. The mixture was partitioned between aqueous sodium bicarbonate and methylene chloride. The organic layer was separated, dried (sodium sulfate) and concentrated in vacuo. The crude material was purified by flash chromatography (silica, 1:19 then 1:4 EtOAc/hexane) to give 60 mg (29%) of Part F compound as a yellow oil.

G. 4-Butoxy-5-thiophenyl-1H-pyrazolo[3,4-b]pyridine.

A solution of 60 mg (0.15 mmol) of Part F compound in 1 mL of trifluoroacetic acid was heated to 65° C. for 2.5 hr then cooled to room temperature and concentrated in vacuo. An aqueous saturated sodium bicarbonate solution was added to the residue. The solid which formed was collected by filtration then recrystallized (EtOAc/hexane) to afford 28 mg (62%) of Part G compound.

H. 1-(4-Butoxy-1H-pyrazolo[3,4-b]pyridin-5-yl)-1'-phenylsulfoxide.

To a solution of 9 mg (0.03 mmol) of Part G compound in 15 mL of methylene chloride cooled in an ice-bath was added 6 mg (tech 80%, 0.03 mmol) of m-chloroperoxybenzoic acid. The reaction mixture was stirred for 40 minutes then aqueous sodium bicarbonate solution was added and extracted with methylene chloride. The organic extract was dried (sodium sulfate) and concentrated in vacuo to give the crude product. Crystallization (EtOAc/hexane) of the crude material afforded 7 mg (74%) of the title compound as a yellow solid.

LC-MS: 316 (M+H)$^+$.

HPLC: $T_R$ (YMC S3 ODS-A, 150×6.0 mm, 1.5 mL/min, gradient 0–100%B over 20 min, Buffer A=MeOH/water/phosphoric acid (10:90:0.2), Buffer B=MeOH/water/phosphoric acid (90:10:0.2))=18.5 min, 88% of total peak area at 220 nM.

Example 2

1-(4-Butoxy-1H-pyrazolo[3,4-b]pyridin-5-yl)-1'-phenylsulfone

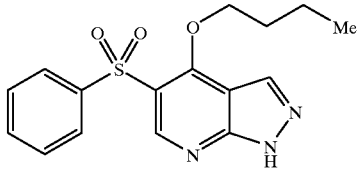

A. 1-(4-Butoxy-1H-pyrazolo[3,4-b]pyridin-5-yl)-1'-phenylsulfone

To a solution of 28 mg (0.094 mmol) of Example 1, Part G compound in 25 mL of methylene chloride at room temperature was added 56 mg (tech 80%, 0.26 mmol) of m-chloroperoxybenzoic acid. The reaction mixture was stirred for 1 hr, aqueous sodium bicarbonate solution was added then after 2 hr the mixture was dried (sodium sulfate) and concentrated in vacuo to give the crude product. Crystallization (methylene chloride/hexane) of the crude material afforded 24 mg (78%) of the title compound as a white solid. LC-MS: 332 (M+H)$^+$.

HPLC: $T_R$ (YMC S3 ODS-A, 150×6.0 mm, 1.5 mL/min, gradient 0–100%B over 20 min, Buffer A=MeOH/water/phosphoric acid (10:90:0.2), Buffer B=MeOH/water/phosphoric acid (90:10:0.2))=18.1 min, 90% of total peak area at 220 nM.

What is claimed is:

1. A compound of formula I:

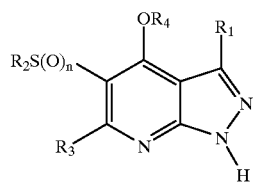

(I)

or a pharmaceutically acceptable salt thereof wherein;
$R_1$ is hydrogen, lower alkyl, Cl;
each $R_2$ and $R_4$ is, independently alkyl, aryl, arylalkyl, heteroaryl, heteroarylalkyl, cycloalkyl, cycloalkylalkyl, heterocycloalkyl or heterocycloalkylalkyl;
$R_3$ is hydrogen or lower alkyl; and
n is 1.

2. The compound according to claim 1 wherein:
$R_1$ and $R_3$ are hydrogen;
$R_2$ is phenyl, 4-bromo-2,6-difluorophenyl, 4-chloro-2,6-difluorophenyl or 2,4,6-trifluorophenyl or 4-methyl-2,6-difluorophenyl;
$R_4$ is lower alkyl; and
n is 1.

3. A pharmaceutical composition comprising a compound of claim 1 and a pharmaceutically acceptable carrier.

4. A pharmaceutical composition comprising a compound of formula I

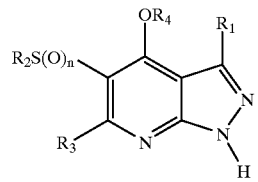

(I)

or a pharmaceutically acceptable salt thereof wherein;
$R_1$ is hydrogen, lower alkyl, Cl;
each $R_2$ and $R_4$ is, independently alkyl, aryl, arylalkyl, heteroaryl, heteroarylalkyl, cycloalkyl, cycloalkylalkyl, heterocycloalkyl or heterocycloalkylalkyl;
$R_3$ is hydrogen or lower alkyl; and
n is 0, 1, or 2;
in combination with a pharmaceutically acceptable carrier and an anti-cancer agent formulated as a fixed dose.

5. A pharmaceutical composition as in claim 4, wherein said anti-cancer agent ia a modulator of p53 transactivation.

6. A method of modulating apoptosis comprising administering to a mammalian specie in need thereof an effective apoptosis modulating amount of a compound of formula I:

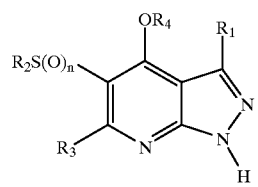

(I)

or a pharmaceutically acceptable salt thereof wherein;
$R_1$ is hydrogen, lower alkyl, Cl;
each $R_2$ and $R_4$ is, independently alkyl, aryl, arylalkyl, heteroaryl, heteroarylalkyl, cycloalkyl, cycloalkylalkyl, heterocycloalkyl or heterocycloalkylalkyl;
$R_3$ is hydrogen or lower alkyl; and
n is 0, 1, or 2.

7. A method of inhibiting protein kinases comprising administering to a mammalian specie in need thereof an effective protein kinase inhibiting amount of a compound of formula I:

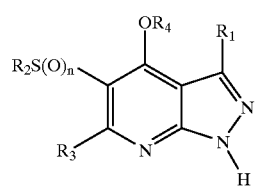

(I)

or a pharmaceutically acceptable salt thereof within;
$R_1$ is hydrogen, lower alkyl, Cl;
each $R_2$ and $R_4$ is, independently alkyl, aryl, arylalkyl, heteroaryl, heteroarylalkyl, cycloalkyl, cycloalkylalkyl, heterocycloalkyl or heterocycloalkylalkyl;
$R_3$ is hydrogen or lower alkyl; and
n is 0, 1, or 2.

8. A method for treating proliferative diseases comprising administering to a mammalian specie in need thereof a therapeutically effective amount of a composition of formula I:

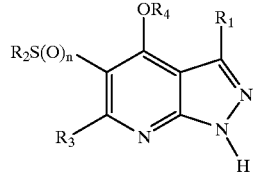

(I)

or a pharmaceutically acceptable salt thereof wherein;
$R_1$ is hydrogen, lower alkyl, Cl;
each $R_2$ and $R_4$ is, independently alkyl, aryl, arylalkyl, heteroaryl, heteroarylalkyl, cycloalkyl, cycloalkylalkyl, heterocycloalkyl or heterocycloalkylalkyl;
$R_3$ is hydrogen or lower alkyl; and
n is 0, 1, or 2.

9. The method of claim 8, wherein said proliferative disease is cancer.

10. A method for treating inflammation, inflamatory bowel disease, or transplantation rejection, comprising administering to a mammalian specie in need thereof a therapeutically effective amount of a composition of claim 3.

11. A method for treating arthritis comprising administering to a mammalian specie in need thereof a therapeutically effective amount of a composition of claim 3.

12. A method for treating proliferative diseases comprising administering to a mammalian specie in need thereof a therapeutically effective amount of a composition of claim 4.

13. A method for treating cancer comprising administering to a mammalian specie in need thereof a therapeutically effective amount of a composition of claim 4.

14. A method for treating proliferative diseases comprising administering to a mammalian specie in need thereof a therapeutically effective amount of a composition of claim 5.

15. A method for treating cancer comprising administering to a mammalian specie in need thereof a therapeutically effective amount of a composition of claim 5.

16. A method for the treatment of a cyclin dependent kinase-associated disorder comprising administering to a subject in need thereof an amount effective therefor of at least one compound of formula I:

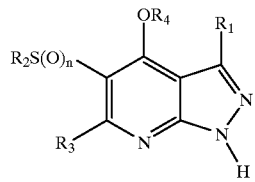

(I)

or a pharmaceutically acceptable salt thereof wherein;
$R_1$ is hydrogen, lower alkyl, Cl;
each $R_2$ and $R_4$ is, independently alkyl, aryl, arylalkyl, heteroaryl, heteroarylalkyl, cycloalkyl, cycloalkylalkyl, heterocycloalkyl or heterocycloalkylalkyl;
$R_3$ is hydrogen or lower alkyl; and
n is 0, 1, or 2.

17. A method for treating chemotherapy-induced alopecia, chemotherapy-induced thrombocytopenia, chemotherapy-induced leukopenia or mucocitis comprising administering to a mammalian specie in need thereof a therapeutically effective amount of a compound of formula I:

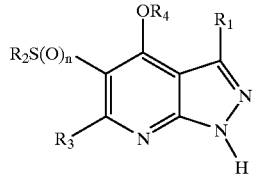

(I)

or a pharmaceutically acceptable salt thereof wherein;
$R_1$ is hydrogen, lower alkyl, Cl;
each $R_2$ and $R_4$ is, independently alkyl, aryl, arylalkyl, heteroaryl, heteroarylalkyl, cycloalkyl, cycloalkylalkyl, heterocycloalkyl or heterocycloalkylalkyl;
$R_3$ is hydrogen or lower alkyl; and
n is 0, 1, or 2.

18. A compound of formula I:

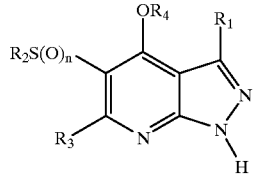

(I)

or a pharmaceutically acceptable salt thereof wherein;
$R_1$ is hydrogen, lower alkyl, Cl;
each $R_2$ and $R_4$ is, independently alkyl, aryl, arylalkyl, heteroaryl, heteroarylalkyl, cycloalkyl, cycloalkylalkyl, heterocycloalkyl or heterocycloalkylalkyl;
$R_3$ is hydrogen or lower alkyl; and
n is 0, 1, or 2.

19. A compound of formula I:

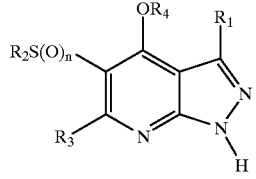

(I)

or a pharmaceutically acceptable salt thereof wherein;
$R_1$ is hydrogen, lower alkyl, Cl;
each $R_2$ is, independently alkyl, aryl, arylalkyl, heteroaryl, heteroarylalkyl, cycloalkyl, cycloalkylalkyl, heterocycloalkyl or heterocycloalkylalkyl;
$R_4$ is, independently $C_8$–$C_{12}$ alkyl, aryl, arylalkyl, heteroaryl, heteroarylalkyl, cycloalkyl, cycloalkylalkyl, heterocycloalkyl or heterocycloalkylalkyl;
$R_3$ is hydrogen or lower alkyl; and
n is 0, 1, or 2.

20. A compound of formula I:

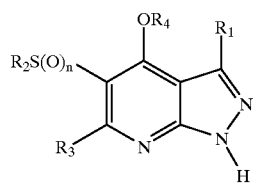

or a pharmaceutically acceptable salt thereof wherein;

$R_1$ is hydrogen, lower alkyl, Cl;

each $R_2$ is, independently alkyl, aryl, arylalkyl, heteroaryl, heteroarylalkyl, cycloalkyl, cycloalkylalkyl, heterocycloalkyl or heterocycloalkylalkyl;

$R_4$ is $C_8$–$C_{12}$;

$R_3$ is hydrogen or lower alkyl; and n is 0 or 2.

21. The method of claim 7 wherein said protein kinase is a cyclin dependent kinase.

22. The method of claim 7 wherein said protein kinase is cdc2 (cdk1).

23. The method of claim 7 wherein said protein kinase is cdk2.

24. The method of claim 7 wherein said protein kinase is cdk3.

25. The method of claim 7 wherein said protein kinase is cdk4.

26. The method of claim 7 wherein said protein kinase is cdk5.

27. The method of claim 7 wherein said protein kinase is cdk6.

28. The method of claim 7 wherein said protein kinase is cdk7.

29. The method of claim 7 wherein said protein kinase is cdk8.

* * * * *